United States Patent
Donate et al.

(10) Patent No.: US 9,277,912 B2
(45) Date of Patent: Mar. 8, 2016

(54) SYSTEMS AND METHODS FOR ANKLE SYNDESMOSIS FIXATION

(75) Inventors: Guillermo Donate, Tampa, FL (US); Melissa Abercrombie, Wesley Chapel, FL (US)

(73) Assignees: University of South Florida, Tampa, FL (US); The United States Government as Represented by the Department of Veterans Affairs, Washington, DC (US)

( * ) Notice: Subject to any disclaimer, the term of this patent is extended or adjusted under 35 U.S.C. 154(b) by 583 days.

(21) Appl. No.: 13/523,246

(22) Filed: Jun. 14, 2012

(65) Prior Publication Data
US 2013/0030480 A1    Jan. 31, 2013

Related U.S. Application Data

(60) Provisional application No. 61/496,690, filed on Jun. 14, 2011.

(51) Int. Cl.
*A61B 17/04* (2006.01)
*A61B 17/80* (2006.01)

(52) U.S. Cl.
CPC ............ *A61B 17/0401* (2013.01); *A61B 17/80* (2013.01); *A61B 2017/0409* (2013.01); *A61B 2017/0412* (2013.01); *A61B 2017/0437* (2013.01); *A61B 2017/0462* (2013.01)

(58) Field of Classification Search
CPC .................. A61B 17/0401; A61B 2017/0412; A61B 2017/0409; A61B 2017/0462; A61B 2017/0464; A61B 17/0487; A61B 2017/0496; A61B 2017/0437
USPC .......... 606/328, 139, 144, 148, 222, 228, 232
See application file for complete search history.

(56) References Cited

U.S. PATENT DOCUMENTS

| | | | |
|---|---|---|---|
| 5,921,986 A * | 7/1999 | Bonutti | 606/60 |
| 5,993,477 A * | 11/1999 | Vaitekunas | A61B 17/0401 606/232 |
| 6,319,252 B1 * | 11/2001 | McDevitt | A61B 17/0401 606/60 |
| 6,716,234 B2 | 4/2004 | Grafton | |
| 7,235,091 B2 * | 6/2007 | Thornes | 606/232 |
| 7,867,251 B2 * | 1/2011 | Colleran et al. | 606/232 |
| 8,323,315 B2 * | 12/2012 | Schwartz et al. | 606/232 |
| 8,696,716 B2 * | 4/2014 | Kartalian et al. | 606/300 |
| 2003/0088270 A1 | 5/2003 | Lubbers | |
| 2003/0236555 A1* | 12/2003 | Thornes | 606/232 |
| 2008/0208252 A1* | 8/2008 | Holmes | A61B 17/0401 606/232 |
| 2008/0262544 A1 | 10/2008 | Burkhart | |
| 2008/0281325 A1* | 11/2008 | Stone et al. | 606/60 |
| 2008/0319478 A1 | 12/2008 | Foerster | |
| 2009/0131936 A1* | 5/2009 | Tipirneni et al. | 606/64 |

(Continued)

OTHER PUBLICATIONS

"Tightrope Syndesmosis Fixation," Surgical Technique, Arthrex; developed in conjuction with Brian Thornes, M.D., Dublin, Ireland, Copyright Arthrex, Inc., 2007.

*Primary Examiner* — Christopher Beccia
*Assistant Examiner* — Diana S Jones
(74) *Attorney, Agent, or Firm* — Thomas | Horstemeyer, LLP (57) ABSTRACT

In one embodiment, a fixation system includes an anchor adapted to be implanted within a first bone, a washer adapted to be associated with a second bone that is to be secured to the first bone, and a suture that is fixedly attached at one end to the anchor and that extends between the anchor and the washer in multiple passes, the suture being adapted to extend through a passage formed in the first and second bones.

19 Claims, 12 Drawing Sheets

(56) References Cited

U.S. PATENT DOCUMENTS

| | | | |
|---|---|---|---|
| 2009/0177199 A1* | 7/2009 | Tipirneni | 606/62 |
| 2009/0198287 A1* | 8/2009 | Chiu | 606/301 |
| 2009/0228049 A1* | 9/2009 | Park | 606/301 |
| 2010/0076504 A1* | 3/2010 | Mcnamara et al. | 606/86 R |
| 2011/0137341 A1* | 6/2011 | Thornes et al. | 606/232 |
| 2011/0306989 A1* | 12/2011 | Darois et al. | 606/144 |
| 2012/0016426 A1* | 1/2012 | Robinson | 606/328 |
| 2012/0089193 A1* | 4/2012 | Stone | A61B 17/0401 606/301 |
| 2012/0165864 A1* | 6/2012 | Hernandez et al. | 606/232 |
| 2012/0283749 A1* | 11/2012 | Sauer | 606/144 |

\* cited by examiner

SYSTEMS AND METHODS FOR ANKLE SYNDESMOSIS FIXATION

CROSS-REFERENCE TO RELATED APPLICATION(S)

This application claims priority to U.S. Provisional Application Ser. No. 61/496,690, filed Jun. 14, 2011, which is hereby incorporated by reference herein in its entirety.

BACKGROUND

When a serious fracture of the ankle occurs, it is common for the syndesmosis ligaments that extend between the fibula and the tibia to be disrupted. In such cases, it is common practice to fix the fibula to the tibia to enable the syndesmosis ligaments to heal. Because the fibula and the tibia move relative to each other during walking and running, the fibula and tibia are typically fixed using a high-strength suture. The suture stabilizes the ankle without preventing the natural relative movement of the bones.

Although the above-described fixation scheme is effective, there are several drawbacks with the current procedures used to achieve that fixation. With current technology, incisions must be made on both sides of the ankle and holes must be drilled entirely through both the fibula and the tibia. In addition, the suture must be manually held under tension while it is manually tied off to complete the fixation. This process often results in unwanted slack being formed in the suture, which reduces the degree of fixation that can be achieved. Furthermore, multiple knots may be required to tie off the suture, and those knots often can be felt and/or seen through the patient's skin.

In view of the above drawbacks, it can be appreciated that it would be desirable to have an alternative system and method for ankle syndesmosis fixation.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for ankle syndesmosis fixation that avoids one or more of the drawbacks of current fixation procedures. Disclosed herein are examples of such systems and methods. In some embodiments, an ankle syndesmosis fixation system comprises an anchor that can be implanted within the tibia and a washer that can be associated with (e.g., implanted within) the fibula. A high-strength suture extends between the anchor and the washer and is threaded through those elements such that, when the suture is pulled, the washer is automatically moved closer to the anchor to fix the fibula to the tibia. In some embodiments, the suture can only pass through the washer in one direction such that the length of the suture extending between the anchor and washer will not slacken when the suture is released. Because of such functionality, the suture can simply be pulled through the washer, tensioned to a desired degree, and cut. Therefore, there is no need to manually maintain the tension in the suture or to tie knots in the suture.

In the following disclosure, various embodiments are described. It is to be understood that those embodiments are merely example implementations of the disclosed inventions and that alternative embodiments are possible. Applicant intends the scope of this disclosure to extend to such embodiments.

Figure 1:
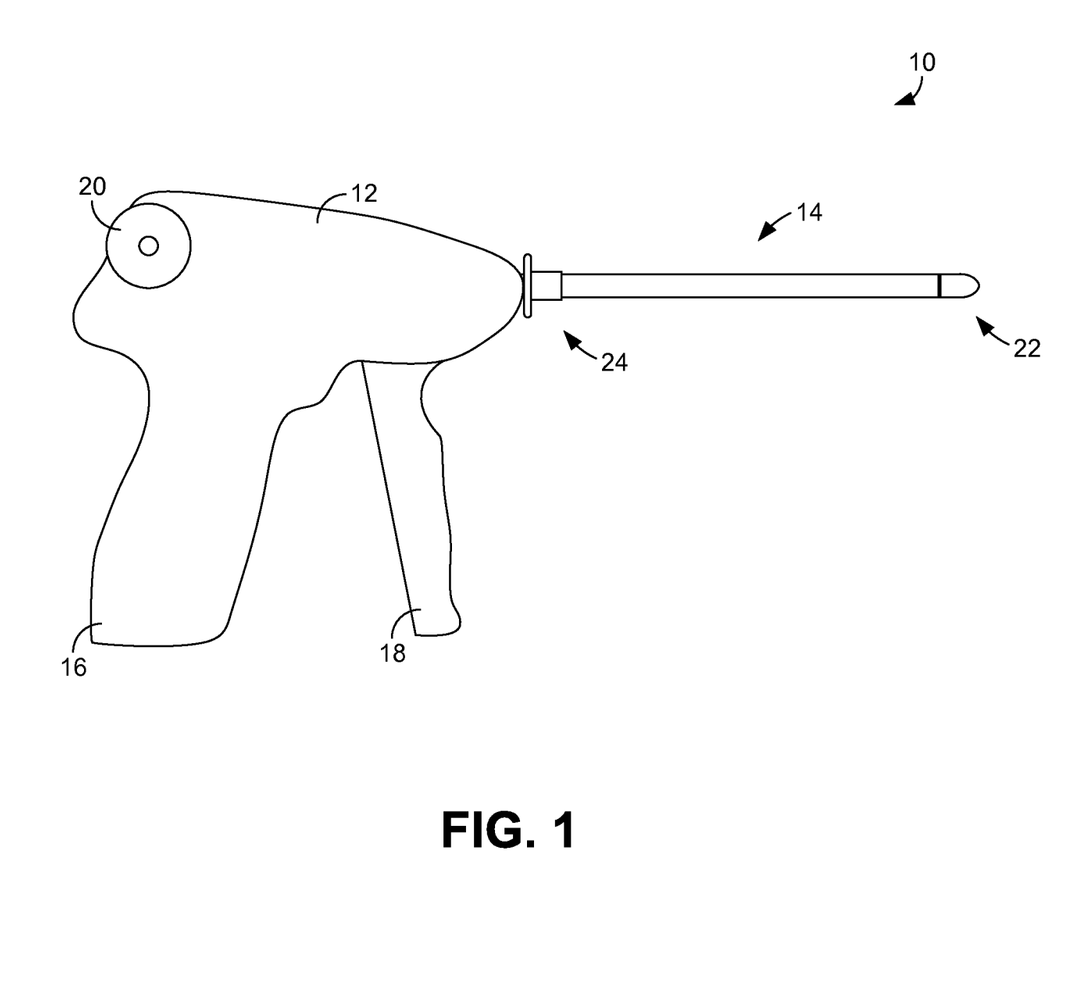
FIG. 1 is a side view of an embodiment of a device for implanting an ankle syndesmosis fixation system.

FIG. 1 illustrates a device 10 that can be used to implant an ankle syndesmosis fixation system. As shown in FIG. 1, the implantation device 10 generally includes a body 12 and a shaft 14. The body 12 is adapted to be gripped by a surgeon or other practitioner. In some embodiments, the body 12 is generally shaped like a handgun and includes a hand grip 16. Mounted to the body 12 are a trigger 18 and a rotatable knob 20. As is described below, the trigger 18 can be used to deploy prongs of an anchor of the ankle syndesmosis fixation system and to release the anchor from the device 10, and the knob 20 can be used to tighten a suture of the fixation system. As is further shown in FIG. 1, the shaft 14 extends forwardly from the body 12 and is long and narrow so that it can pass through a passage formed through the fibula and the tibia. Attached to a distal end of the shaft 14 is an anchor 22 that can be implanted within the tibia. Positioned at a proximal end of the shaft 14 is a washer 24 that can be positioned on the outside of the fibula in alignment with the anchor.

Figures 2, 3A, 3B:
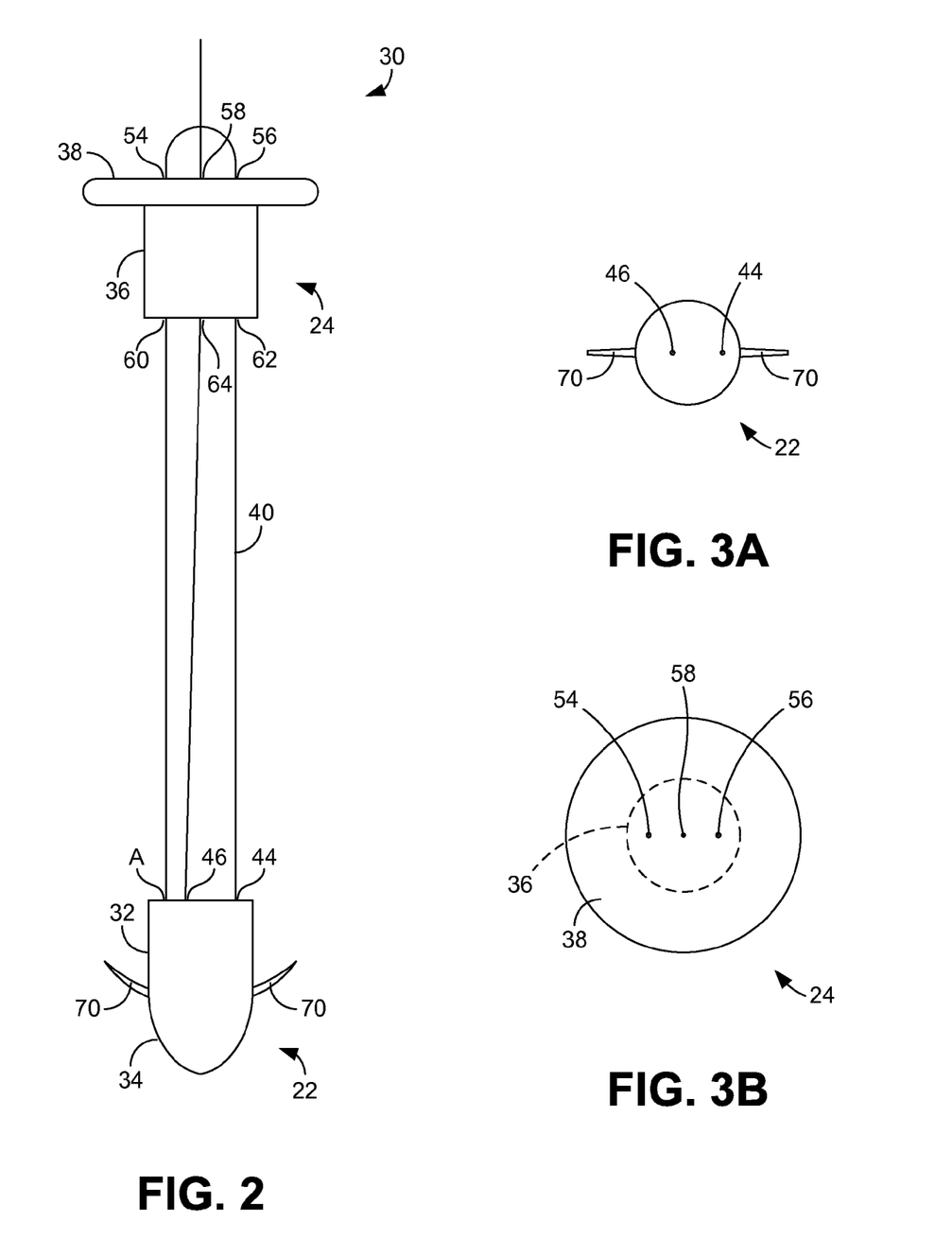
FIG. 2 is a side view of an embodiment of an ankle syndesmosis fixation system.
FIG. 3A is an end view of an anchor of the fixation system of FIG. 2.
FIG. 3B is an end view of a washer of the fixation system of FIG. 2.

FIG. 2 illustrates an embodiment of an ankle syndesmosis fixation system 30 separate from the implantation device 10. As is shown in that figure, the system 30 includes the anchor 22 and the washer 24. The anchor 22, which is also shown in end view in FIG. 3A, can have a generally cylindrical body 32 and a pointed and/or rounded tip 34 that facilitates its passage through the fibula and into the tibia. The size of the anchor 22 is to some degree dictated by the anatomy of the patient. In some embodiments, however, the anchor 22 has a cross-sectional diameter of approximately 3 to 5 millimeters (mm) and a length of approximately 3 to 5 mm. Irrespective of its size, the anchor 22 can be made of a strong, biocompatible material, such as stainless steel or titanium.

The washer 24, which is also shown in end view in FIG. 3B, can have a generally cylindrical body 36 and a circular flange 38 that is positioned at one end of the body. The washer body 36 is sized to fit within the passage formed during the fixation procedure and can also be made of a strong, biocompatible material, such as stainless steel or titanium. Although the washer 24 has been shown and described as having a body and a flange, it is noted that, in other embodiments, the washer can only comprise the flange 38 in which case the washer takes the form of a button. For reasons that are apparent below, however, the presence of the body 36 provides for more secure fixation of the washer 24 relative to the fibula.

With continued reference to FIG. 2, extending between the anchor 22 and the washer 24 are multiple passes of a high-strength suture 40. In some embodiments, the suture 40 comprises a multi-stranded long-chain ultra-high molecular weight polyethylene (UHMWPE) core with a braided jacket of polyester and UHMWPE, such as FiberWire® suture manufactured by Arthrex. Irrespective of the nature of the suture 40, it passes through multiple passages formed through both the anchor 22 and the washer 24. Those passages are shown in FIGS. 4A and 4B.

Figure 4A:
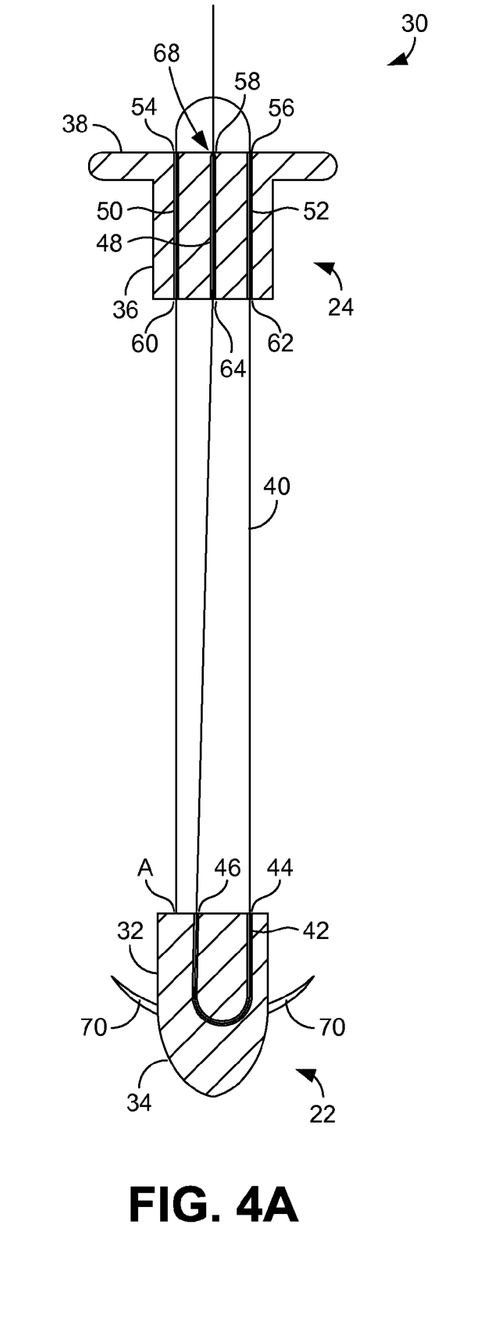
FIG. 4A is cross-sectional view of the fixation system of FIG. 2, with the system shown in an untightened orientation.
Figure 4B:
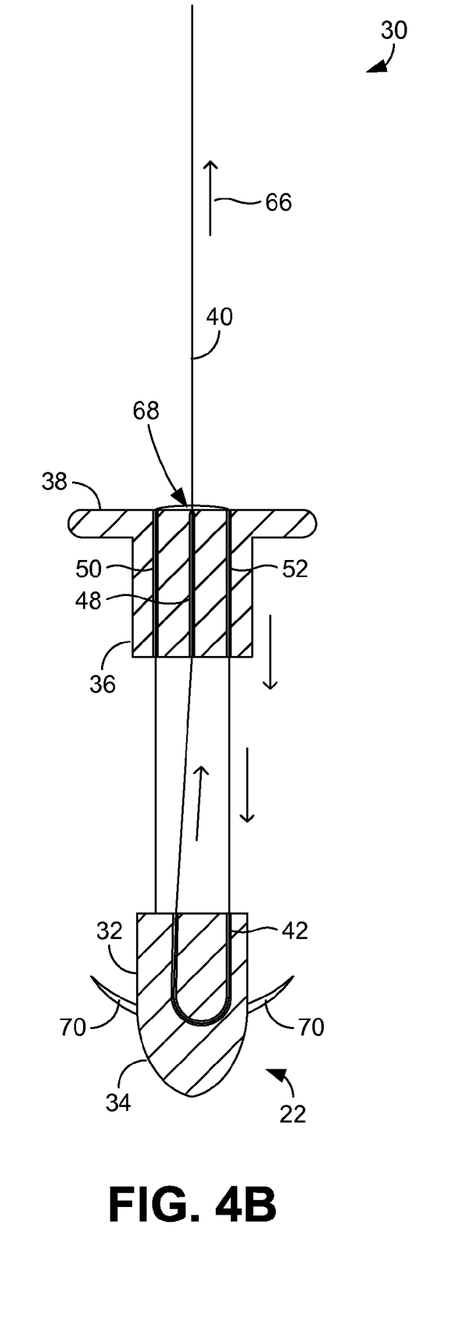
FIG. 4B is cross-sectional view of the fixation system of FIG. 2, with the system shown in a tightened orientation.

Turning to FIG. 4A, there is a continuous U-shaped passage 42 formed through the body 32 of the anchor 22 that can be accessed through openings 44 and 46 formed in the anchor (see also FIG. 3A). Therefore, the passage 42 can be entered through the opening 44, traversed, and exited through opening 46. There are three independent linear, parallel passages formed through the body 36 and flange 38 of the washer 24, including a central passage 48 and two peripheral passages 50 and 52. Those passages can be accessed on one end through openings 54, 56, and 58 (see also FIG. 3B), and on the other end through openings 60, 62, and 64.

With continued reference to FIG. 4A, an end of the suture 40 is fixedly connected to the anchor 22 at a point A. In the illustrated embodiment, the suture 40 extends from the anchor 22 to the washer 24, passes through the passage 50, emerges from the washer, passes through passage 52, emerges from the washer again, extends back to the anchor, passes thorough passage 42, exits the anchor, extends back to the washer, passes through the passage 48, and finally emerges again from the washer. With such a configuration, the suture 40 can be pulled through the washer 24 in the direction indicated by arrow 66 in FIG. 4B (i.e., away from the flange 38). As the suture 40 moves through the passages of the washer 24 and the anchor 22, the washer is pulled closer to the anchor, as is also shown in FIG. 4B.

In some embodiments, at least one of the passages of the washer 24 is a one-way passage such that the suture 40 can only pass through the passage in one direction. By way of example, the passage 48 is a one-way passage that comprises a neck 68 that enables the suture 40 to be pulled in the direction of the arrow 66, but prevents the suture from being pulled in the opposite direction (i.e., toward the anchor). In such a case, the ankle syndesmosis fixation system 30 automatically holds whatever tension that is created by the surgeon by pulling on the suture 40.

As is further illustrated in FIGS. 2, 3A, 4A, and 4B, the anchor 22 also comprises anchoring barbs or prongs 70 that can be deployed when the anchor 22 has been positioned within the tibia. Although the prongs 70 can take various forms, in each case they help fix the anchor 22 in place and prevent it from being dislodged from the tibia.

Figure 5:
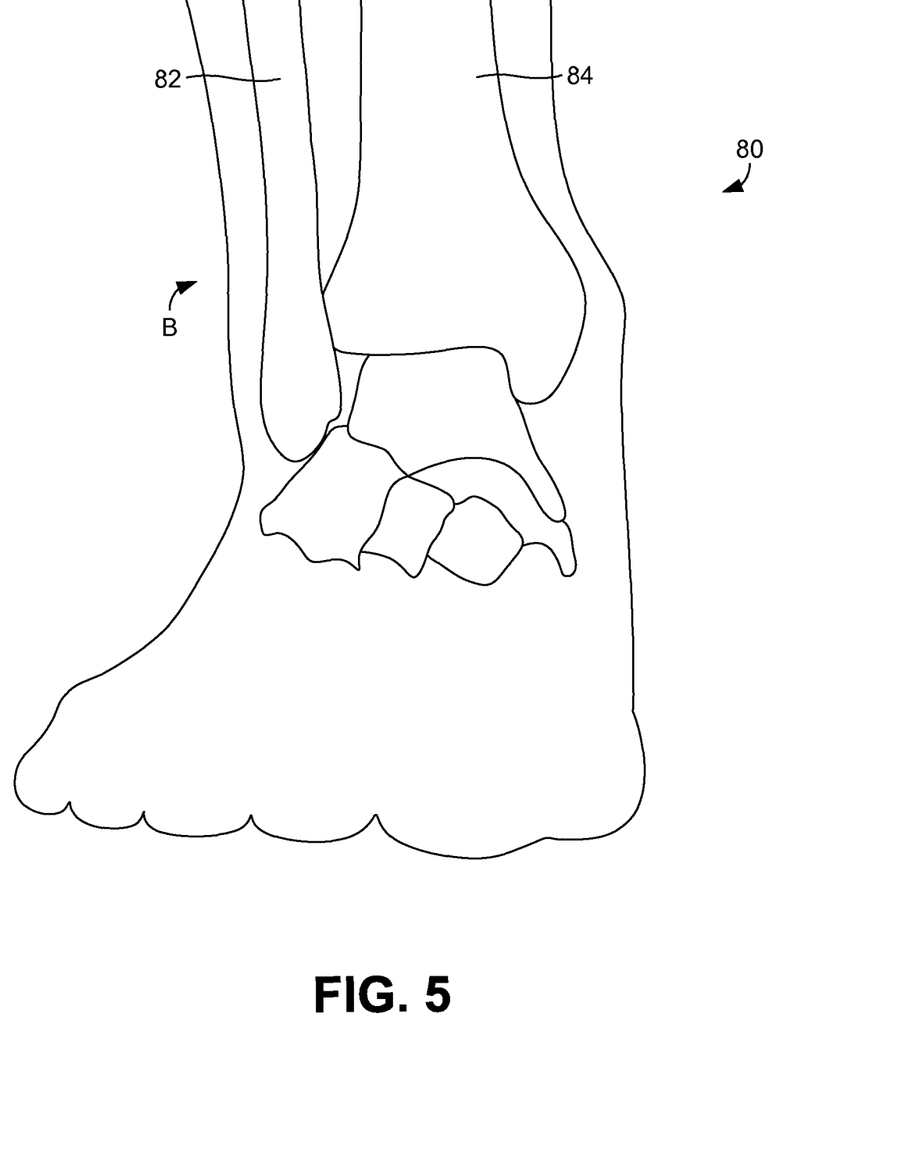
FIG. 5 is an anterior view of a human ankle prior to syndesmosis fixation.

FIG. 5 illustrates an example ankle 80 on which an ankle syndesmosis fixation procedure can be performed. As indicated in FIG. 5, the ankle 80 includes the fibula 82 and the tibia 84. In the fixation procedure, the fibula 82 is to be tightly secured to the tibia 84 without preventing relative movement between the two bones. To begin the procedure, a single incision is made on the outside of the patient's ankle near point B. In cases in which fixation of a concurrent fibular fracture has been performed, an incision may already be present.

Figure 6A:
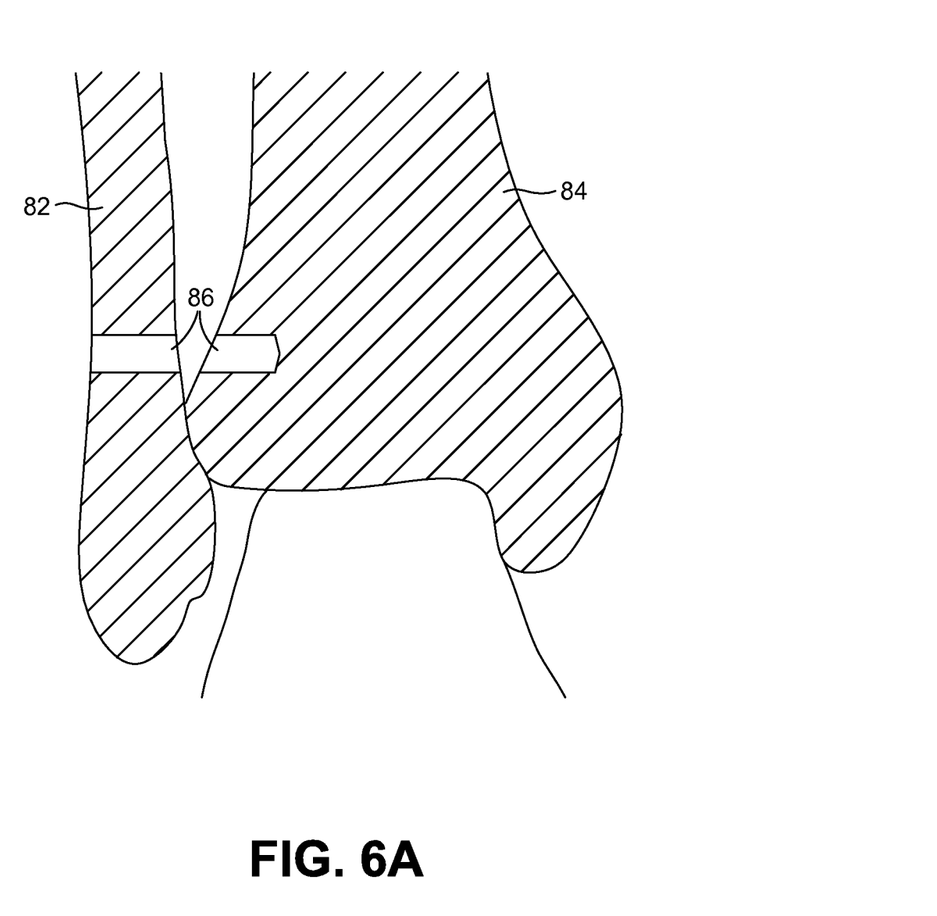
FIGS. 6A-6G are sequential anterior views of the bones of the human ankle of FIG. 4 during an example ankle syndesmosis fixation procedure.

After the incision has been made, a passage 86 is formed through the fibula 82 and the tibia 84, as shown in FIG. 6A. As is indicated in that figure, the passage 86 does not extend all the way through the tibia 84. Instead, the passage 86 extends into the tibia 84 just far enough to provide room for the anchor 22. By way of example, the passage 86 is formed using a drill and is approximately 3 to 5 mm in diameter and extends into the tibia a distance of approximately 10 to 20 mm.

Figure 6B:
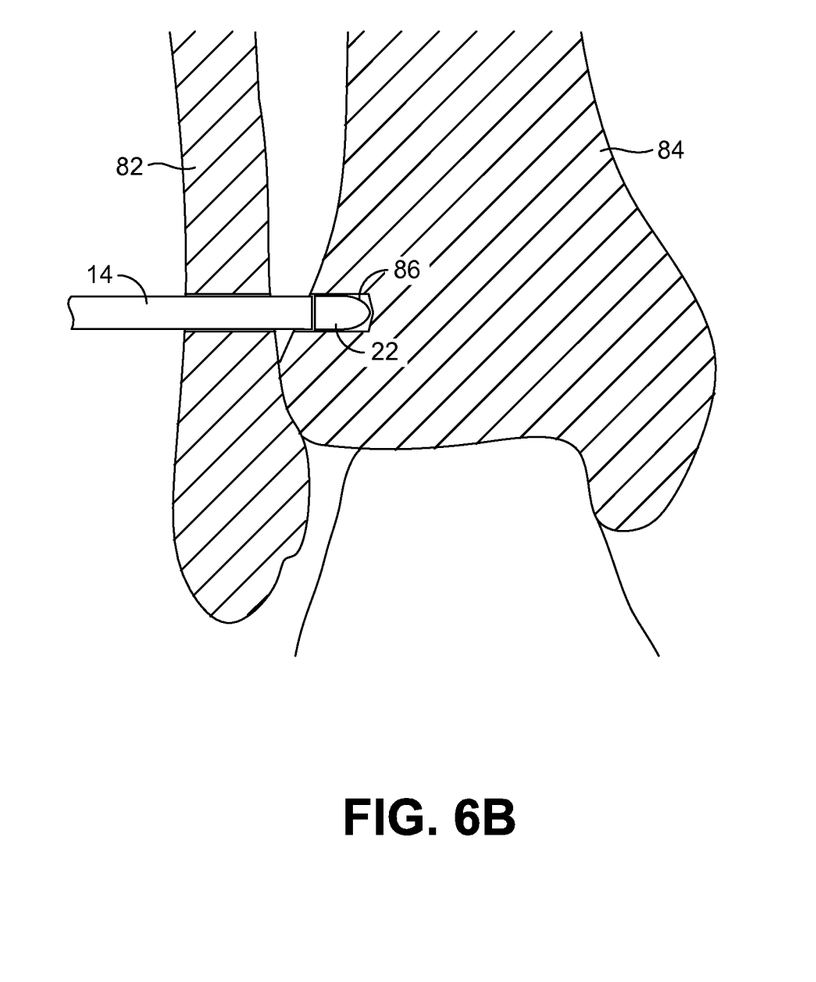

Once the passage 86 has been formed, the anchor 22 can be positioned within the tibia 84 by passing it through the passage 86 using the shaft 14 of the device 10, as shown in FIG. 6B.

Figure 6C:
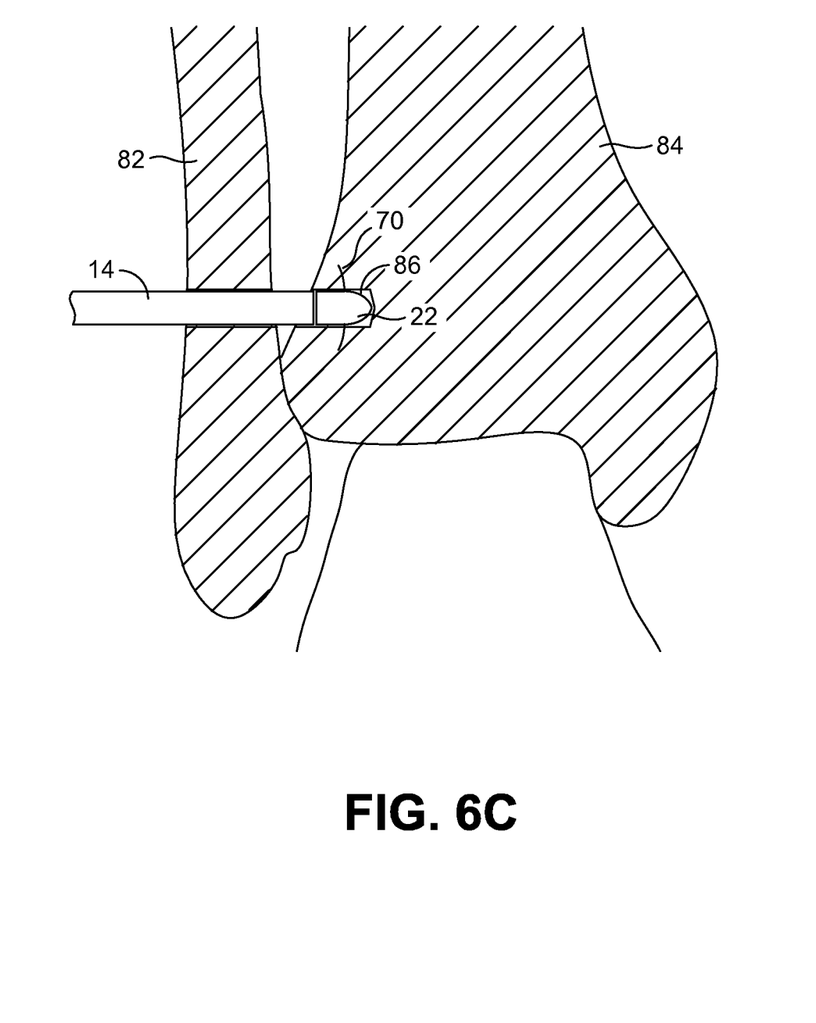

Referring next to FIG. 6C, the prongs 70 of the anchor 22 can be deployed to securely fix the anchor in place within the tibia 84. By way of example, the prongs 70 can be deployed by squeezing the trigger 18 of the device 10.

At this point, the washer 24 can be positioned relative to the fibula 82. In particular, the washer 24 can be pulled in closer to the fibula 82 by pulling the suture 40 in the manner described above in relation to FIG. 4B. By way of example, the suture 40 can be pulled by turning the knob 20 provided on the device 10 to which the suture is attached. In some embodiments, the knob 20 is connected to an internal ratcheting system (not shown) that only enables the knob to turn in a tightening direction in which the suture 40 is pulled (tensioned).

Figure 6D:
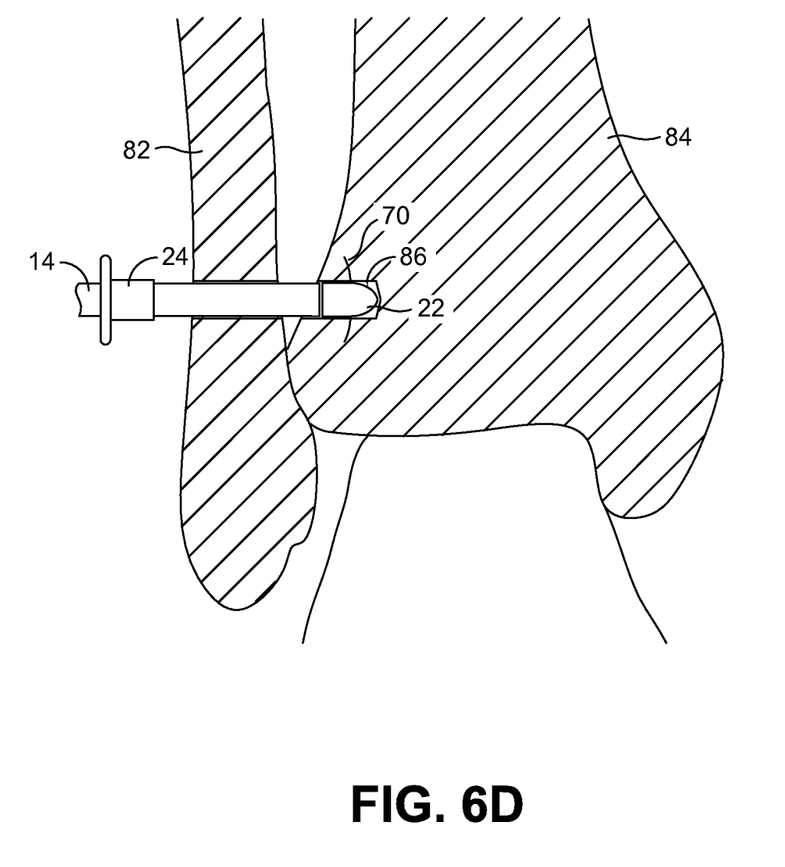
Figure 6E:
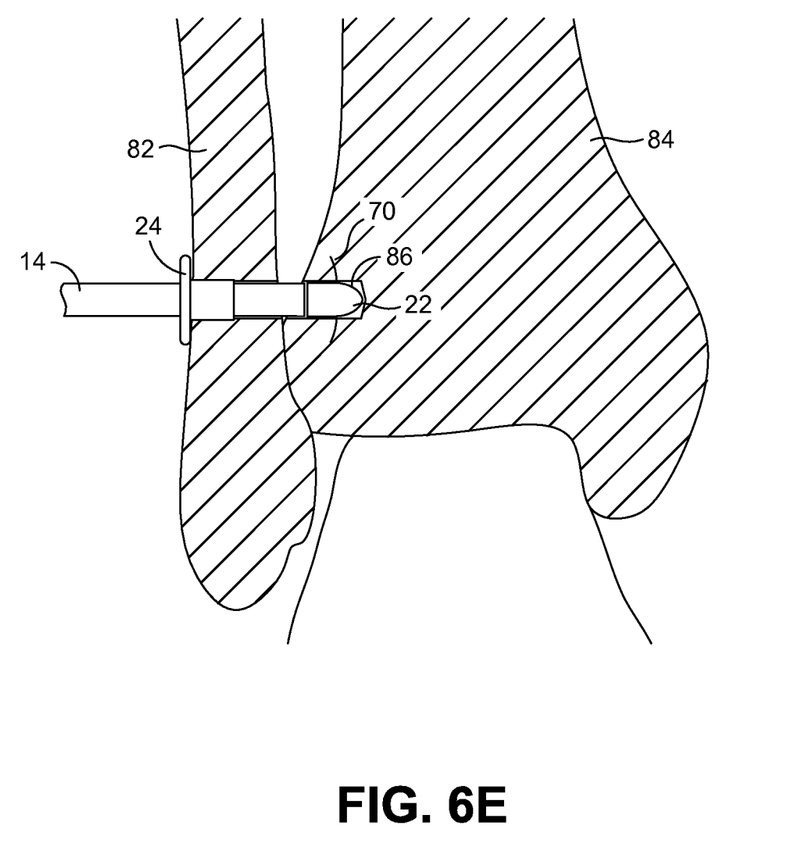
Figure 7:
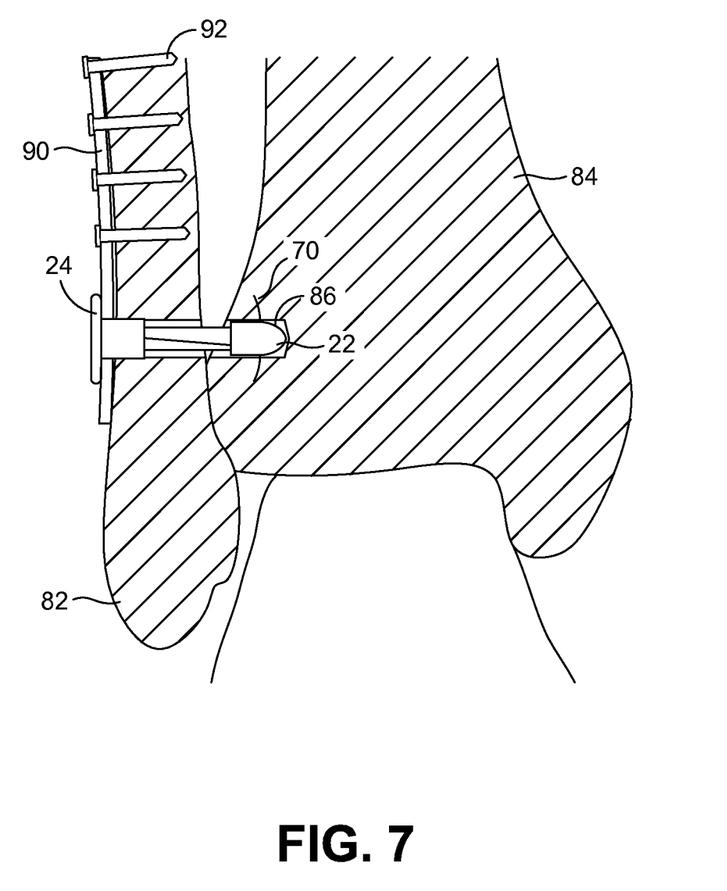
FIG. 7 is an anterior view of the bones of the human ankle after syndesmosis fixation and fibula fixation with a plate.

The washer 24 travels along the shaft 14 toward the fibula 82, as indicated in FIG. 6D, until the body 36 of the washer is positioned within the passage 86 and the flange 38 of the washer abuts the outer side of the fibula 82, as indicated in FIG. 6E. Because the body 36 of the washer 24 fits within the passage 86, the washer will be more stable. Notably, if a plate has already been affixed to the outside of the fibula 82, the washer 24 can pass through a hole formed in the plate and the flange 38 can abut the plate. FIG. 7 illustrates such a situation in which a plate 90 has been secured to the fibula with screws 92. The suture 40 can then be tightened to the appropriate tension. In some embodiments, the suture 40 is tightened with the knob 20 until the surgeon can no longer turn the knob.

Figure 6F:
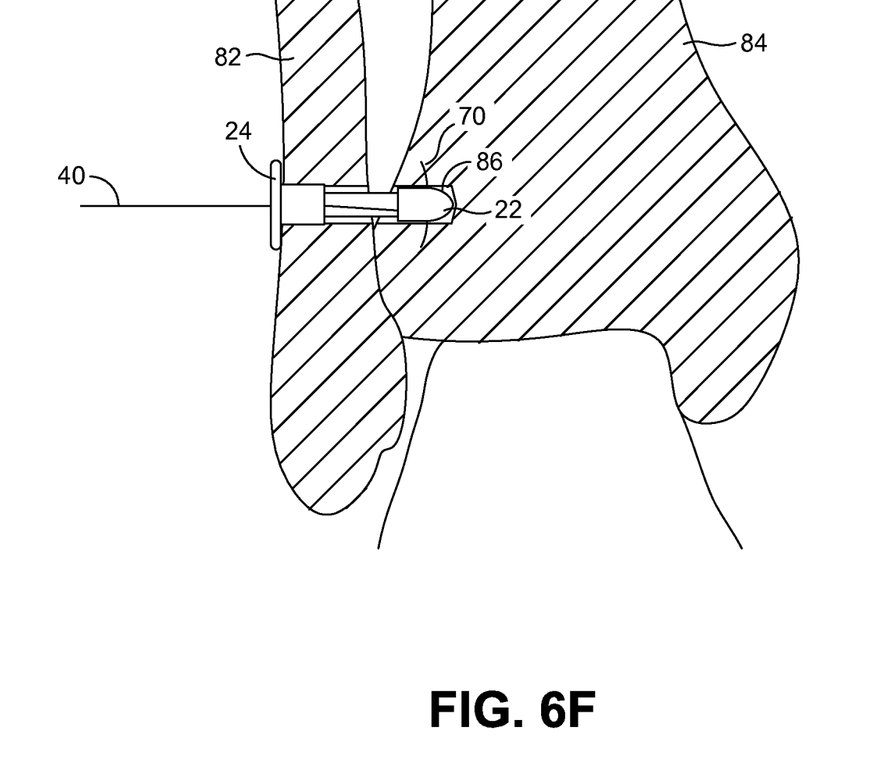
Figure 6G:
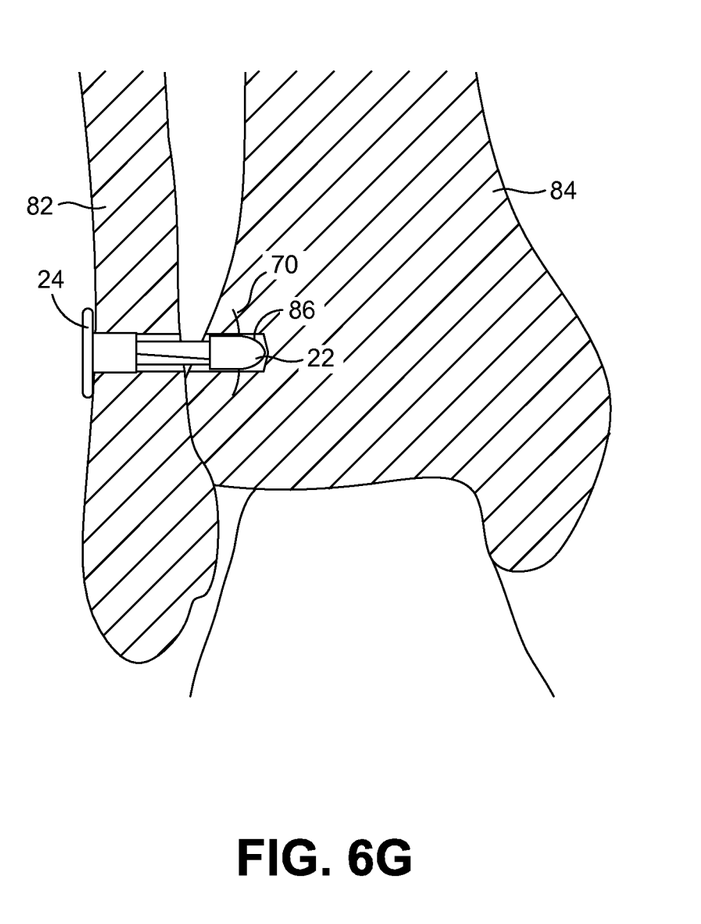

At this point, the anchor 22 can be detached from the shaft 14 of the device 10. In some embodiments, such detachment is achieved by squeezing the trigger 18 a second time. Once the anchor 22 has been detached, the shaft 14 can be withdrawn from the passage 86, as shown in FIG. 6F. Next, the suture 40 can be trimmed. Because the suture 40 can only travel through the washer 24 in the tightening direction, there is no need to manually maintain tension in the suture or to tie knots in the suture. Therefore, the suture 40 can simply be cut adjacent the washer flange 38 as shown in FIG. 6G, which shows the final result of the ankle syndesmosis fixation procedure.

Although this disclosure is focused on the example of ankle syndesmosis fixation, it is noted that the systems and methods could be used in other applications. For example, similar fixation can be in relation to the ulna and radius of the arm.

The invention claimed is:

1. A fixation system comprising:
   an anchor adapted to be implanted within a first bone, the anchor having a body and a pointed or rounded tip;
   a washer adapted to be associated with a second bone that is to be secured to the first bone, the washer having a body that is adapted to be implanted within the second bone and a flange positioned at an end of the washer body that is adapted to be positioned outside of the second bone, the washer further having a one-way passage comprising an integral feature through which a suture can only physically pass in one direction; and
   a suture that is fixedly attached at one end to the anchor and that passes through the one-way passage of the washer, wherein pulling of the suture through the one-way passage pulls the anchor and the washer closer to each other.

2. The system of claim 1, wherein the body of the anchor is generally cylindrical.

3. The system of claim 1, wherein the anchor comprises only one passage through which the suture passes.

4. The system of claim 3, wherein the passage within the anchor is a U-shaped passage.

5. The system of claim 1, wherein the body of the washer is generally cylindrical.

6. The system of claim 1, wherein the washer comprises multiple passages through which the suture passes.

7. The system of claim 1, wherein the suture is a high-strength suture.

8. The system of claim 1, wherein the suture comprises a multi-stranded core surrounded by a braided jacket.

9. The system of claim 1, further comprising an implantation device used to implant the anchor and the washer, the device including an elongated shaft that supports the anchor and washer during the implantation procedure.

10. The system of claim 9, wherein the implantation device comprises a trigger that, when actuated, deploys anchoring prongs of the anchor.

11. The system of claim 9, wherein the implantation device comprises a trigger that, when actuated, releases the anchor from the device.

12. The system of claim 9, wherein the implantation device comprises a knob that, when turned, pulls the suture and thereby moves the washer closer to the anchor.

13. The system of claim 1, wherein the flange of the washer is generally perpendicular to the body of the washer.

14. The system of claim 1, wherein the washer comprises a central passage that extends along a central longitudinal axis of the body and two peripheral passages that are parallel to the central passage.

15. The system of claim 14, wherein the washer comprises no other passages.

16. The system of claim 14, wherein the central passage of the washer is the one-way passage.

17. The system of claim 1, wherein the anchor comprises deployable anchoring prongs can be moved from a position in which they are retracted relative to the anchor body to a position in which they are extended relative the anchor body.

18. The system of claim 1, wherein the integral feature is a neck of the passage.

19. An ankle fixation system comprising:
    an anchor adapted to be implanted within a tibia, the anchor having a cylindrical body, a pointed or rounded tip, and deployable anchoring prongs that can be moved from a position in which they are retracted relative to the body to a position in which they are extended relative to the body;
    a suture that is fixedly attached at one end to the anchor; and
    a washer having a first end and a second end, the washer further having a body that forms the first end and that is adapted to be implanted within a fibula to be secured to the tibia and a flange that forms the second end and that is adapted to be positioned outside of the fibula, the washer further comprising a one-way passage through which a suture can only pass in a direction extending from its first end to its second end, the one-way passage comprising a neck through which the suture can only physically pass in one direction;
    wherein pulling of the suture through the one-way passage pulls the anchor and washer closer to each other.

* * * * *